US010368965B2

(12) United States Patent
Rodrigues et al.

(10) Patent No.: US 10,368,965 B2
(45) Date of Patent: Aug. 6, 2019

(54) SYSTEMS AND METHODS FOR DENTAL ABUTMENTS WITH CEMENT-RETAINED CROWNS

(71) Applicant: Board of Regents, The University of Texas System, Austin, TX (US)

(72) Inventors: Danieli C. Rodrigues, Richardson, TX (US); Lucas C. Rodriguez, Dallas, TX (US); Juliana Saba, Pflugerville, TX (US); Chandur Wadhwani, Woodinville, MA (US)

(73) Assignee: Board of Regents, The University of Texas System, Austin, TX (US)

( * ) Notice: Subject to any disclaimer, the term of this patent is extended or adjusted under 35 U.S.C. 154(b) by 35 days.

(21) Appl. No.: 15/656,202

(22) Filed: Jul. 21, 2017

(65) Prior Publication Data
US 2018/0021109 A1 Jan. 25, 2018

Related U.S. Application Data

(60) Provisional application No. 62/365,638, filed on Jul. 22, 2016.

(51) Int. Cl.
*A61C 8/00* (2006.01)
(52) U.S. Cl.
CPC .......... *A61C 8/0054* (2013.01); *A61C 8/0022* (2013.01); *A61C 8/0048* (2013.01); *A61C 8/0068* (2013.01)
(58) Field of Classification Search
CPC .. A61C 3/32; A61C 8/00; A61C 8/005; A61C 8/003; A61C 8/0039; A61C 8/0048; A61C 8/0065; A61C 8/0068; A61C 8/0071; A61C 8/0075; A61C 8/0078;
(Continued)

(56) References Cited

U.S. PATENT DOCUMENTS 5,071,345 A * 12/1991 Rosen ...................... A61C 7/00
433/17
5,897,320 A 4/1999 Gittleman
(Continued)

OTHER PUBLICATIONS

A finite elements analysis of novel vented dental abutment geometries for cement-retained crown restorations. Lucas C. Rodriguez, Juliana N. Saba, Clark A. Meyer, Kwok-Hung Chun, Chandur Wadhwan, Danieli C. Rodrigues Clinical and Experimental Dental Research Published online Jun. 14, 2016.*
(Continued)

*Primary Examiner* — Wade Miles
*Assistant Examiner* — Matthew P Saunders
(74) *Attorney, Agent, or Firm* — Parker Highlander PLLC

(57) ABSTRACT

Devices and methods for dental abutments. Particular embodiments include a dental abutment comprising a base portion, and a generally cylindrical neck portion extending from the base portion, where the generally cylindrical neck portion comprises a first end proximal to the base portion, a second end distal from the base portion, an outer surface, and an inner surface forming a central lumen. Certain embodiments include a plurality of vent holes extending from the outer surface of the generally cylindrical neck portion to the central lumen, where the plurality of vent holes are located proximal to the base portion of the abutment.

18 Claims, 8 Drawing Sheets

(58) Field of Classification Search
CPC ..... A61C 8/0054; A61C 13/01; A61C 13/083; A61C 13/225; A61C 5/30
USPC .................................................. 433/173–183
See application file for complete search history.

(56) References Cited

U.S. PATENT DOCUMENTS

| | | | | |
|---|---|---|---|---|
| 6,290,500 | B1* | 9/2001 | Morgan | A61C 8/0048 433/173 |
| 6,824,386 | B2* | 11/2004 | Halldin | A61C 8/0001 433/173 |
| 6,910,891 | B2 | 6/2005 | Carroll | |
| 7,059,854 | B2 | 6/2006 | Wu | |
| 2004/0121285 | A1* | 6/2004 | Wu | A61C 8/005 433/173 |
| 2014/0212845 | A1* | 7/2014 | Wadhwani | A61C 13/08 433/174 |
| 2015/0335403 | A1* | 11/2015 | Iijima | A61C 8/006 433/75 |

OTHER PUBLICATIONS

Effect of implant abutment modification on the extrusion of excess cement at the crown-abutment margin for cement-retained implant restorations. Wadhwani, C., Piñeyro, A., Hess, T., Zhang, H., Chung, K.H., Journal of Oral & Maxillofacial implants, vol. 26, No. 6, pp. 1241-1246, 2011.*

Patel, Dipan, et al. "An Analysis of the Effect of a Vent Hole on Excess Cement Expressed at the Crown-Abutment Margin for Cement-Retained Implant Crowns." Journal of Prosthodontics: Implant, Esthetic and Reconstructive Dentistry 18. pp. 54-59, 2009 (Year: 2009).*

Wadhwani, Chandur, Sabine Goodwin, and Kwok-Hung Chung. "Cementing an implant crown: a novel measurement system using computational fluid dynamics approach." Clinical implant dentistry and related research 18.1, pp. 97-106, 2014 (Year: 2014).*

Chee, Winston WL, et al. "Evaluation of the amount of excess cement around the margins of cement-retained dental implant restorations: the effect of the cement application method." *The Journal of prosthetic dentistry* 109.4, pp. 216-221, 2013.

Patel, Dipan, et al. "An Analysis of the Effect of a Vent Hole on Excess Cement Expressed at the Crown—Abutment Margin for Cement-Retained Implant Crowns." *Journal of Prosthodontics: Implant, Esthetic and Reconstructive Dentistry* 18.1, pp. 54-59, 2009.

Rodriguez, Lucas C., et al. "A finite element analysis of novel vented dental abutment geometries for cement-retained crown restorations." *Clinical and experimental dental research* 2.2, pp. 136-145, 2016.

Rodriguez, Lucas Carlos. *Design and Development of a New Dental Abutment System for Cement-retained Crowns*. Diss. University of Texas at Dallas, pp. 1-129, 2016.

Wadhwani, Chandur, et al. "Effect of implant abutment modification on the extrusion of excess cement at the crown-abutment margin for cement-retained implant restorations." *International Journal of Oral & Maxillofacial Implants* 26.6 pp. 1241-1246, 2011.

Wadhwani, Chandur, Sabine Goodwin, and Kwok-Hung Chung. "Cementing an implant crown: a novel measurement system using computational fluid dynamics approach." *Clinical implant dentistry and related research* 18.1, pp. 97-106, 2016.

* cited by examiner

SYSTEMS AND METHODS FOR DENTAL
ABUTMENTS WITH CEMENT-RETAINED
CROWNS

CROSS-REFERENCE TO RELATED APPLICATIONS

This application claims priority to U.S. Provisional Patent Application Ser. No. 62/365,638 filed Jul. 22, 2016, the entire contents of which are incorporated herein by reference.

BACKGROUND INFORMATION

When a dental prosthesis (e.g. a crown) is cemented onto an implant abutment, cements are typically loaded into the intaglio portion of the crown and placed onto the abutment for fixation. It is not uncommon for excess cement to flow out of the abutment-crown margin. This can require a clinician spending time cleaning around the margin in an attempt to remove any remaining cement particles or remnants. Unfortunately, this cleaning procedure is tedious and time consuming as dental cements, once completely set on metallic and ceramic surfaces such as those of implants and crowns, are difficult to remove. Such excess cement can act as a dental calculus or plaque, which can facilitate the development of peri-implant disease.

Peri-implant disease is defined as an inflammatory reaction of the tissues which surround a dental implant system and is known to result in the destruction of bone tissue, ultimately leading to implant failure (American Academy of Periodontology 2013). Peri-implant mucositis refers to inflammation of soft tissues (gum inflammation) surrounding dental implants without signs of bone loss. If this inflammatory process is not controlled, it can develop into peri-implantitis, which is characterized as bone resorption surrounding the implant. The lack of cement placement technique standardization in cement-retained prostheses procedures has only exacerbated the deleterious effect of residual cement induced peri-implant disease (Wadhwani 2015). Clinicians and dental technicians are typically not trained in the placement of dental cements, or the volume of cements needed for these procedures. Reports indicate that peri-implant mucositis is present in nearly fifty percent of implant procedures between 1 month and 10 years (Fransson et al. 2005; Roos-Jansaker et al. 2006). However, this stage of the disease is reversible with early intervention including the removal of residual cement. The reversal of inflammation following the complete cleaning of residual cement lends itself to the hypothesis that the cement components are the cause of the inflammatory reaction surrounding the implant. The prevalence of peri-implant disease in the United States has been recently reported to be between 28 percent and 50 percent. (Zitzmann and Berglundh 2008). Considering the number of implants used per year (between 100,000 and 300,000), this becomes a significant number of peri-implant cases (Gaviria et al. 2014).

Dental cements for cement-retained restorations are often chosen based on clinician preference for the product's material properties, mixing process, delivery mechanism, or viscosity. It has been recently suggested that the composition of the dental cement can play a significant role in the proliferation or inhibition of different bacterial strains associated with peri-implant disease (Raval et al. 2015; Rodriguez et al. 2016a). The effect of dental cements on host cellular proliferation may provide further insight into appropriate cement material selection. As mentioned, recent literature indicates that the long-term success of dental implants is, in part attributed to how dental crowns are attached to their associated implants (Chaar, Att, and Strub 2011; Ma and Fenton 2015; Wismeijer et al. 2014; Wittneben, Millen, and Bragger 2014). The commonly utilized method for crown attachment—cementation—has been criticized due to recent links between residual cement and peri-implant disease (Wilson 2009; Linkevicius et al. 2011; Linkevicius et al. 2012).

These facts make residual cement extrusion from crown-abutment margins post-crown seating a growing concern in the dental community (Wilson 2009; Linkevicius et al. 2011; Linkevicius et al. 2012). While the mechanism of action of residual cement induced peri-implant disease is still being investigated, recent evidence suggests that dental cement components themselves could initiate an inflammatory reaction (Raval et al. 2015; Rodriguez et al. 2016).

As discussed in further detail below, exemplary embodiments of the present disclosure address shortcomings of existing systems and provide notable benefits in comparison to such systems.

SUMMARY

Exemplary embodiments of the present disclosure comprise devices, systems and methods for dental abutments. Exemplary embodiments include a dental implant system comprising vent holes or channels surrounding the abutment neck to improve and direct cement flow during the crown seating procedure. Particular features of exemplary embodiments are designed to reduce the risk of excess cement extrusion during crown seating procedures while retaining mechanical stability for the oral environment.

Exemplary embodiments include a dental abutment comprising a base portion, and a generally cylindrical neck portion extending from the base portion, where the generally cylindrical neck portion comprises: a first end proximal to the base portion; a second end distal from the base portion; an outer surface; and an inner surface forming a central lumen. Exemplary embodiments may further comprise a plurality of vent holes extending from the outer surface of the generally cylindrical neck portion to the central lumen, where the plurality of vent holes are located proximal to the base portion of the abutment.

In certain embodiments, the plurality of vent holes are directly adjacent to the base portion of the abutment. In particular embodiments, the plurality of vent holes are tangential to the base portion of the abutment. In specific embodiments, the generally cylindrical neck portion comprises a length extending from the first end to the second end; and a distance between the first end and a center of a vent hole in the plurality of vent holes is less than twenty percent of the length of the generally cylindrical neck portion.

In some embodiments, the generally cylindrical neck portion comprises a length extending from the first end to the second end; and a distance between the first end and a center of a vent hole in the plurality of vent holes is less than ten percent of the length of the generally cylindrical neck portion. In certain embodiments, the plurality of vent holes comprises vent holes with a diameter between 0.5 mm and 1.0 mm, or more particularly a diameter between 0.6 mm and 0.9 mm. In particular embodiments, the plurality of vent holes comprises vent holes with a diameter of approximately 0.7 mm.

In some embodiments, the plurality of vent holes comprises at least four vent holes, and in specific embodiments the plurality of vent holes comprises at least eight vent holes. In certain embodiments, the first end of the generally cylindrical neck portion has a first diameter; the second end of the generally cylindrical neck portion has a second diameter; and the first diameter is between 1.0 and 1.10 times the second diameter.

Exemplary embodiments include a system comprising: an abutment as described herein (including, for example an abutment according to any of claims 1-11); a dental implant; an abutment screw configured to couple the abutment to the dental implant; and a crown configured to couple to the abutment. In certain embodiments, the abutment screw comprises a first end configured to thread into the dental implant; the abutment screw comprises a second end opposite the first end; and the system further comprises a tapered insert configured to engage the second end of the abutment screw.

In particular embodiments, the crown comprises an interior cavity having a first volume; the central lumen and the plurality of vent holes have a second combined volume; and the first volume is between 1.0 and 1.2 times the second combined volume.

Exemplary embodiments include a method of coupling a dental crown to an abutment, where the method comprises: obtaining a dental crown comprising an interior cavity; placing cement in the interior cavity of the dental crown; and coupling the dental crown to an abutment as described herein (including, for example an abutment according to any of claims 1-11) by engaging the interior cavity of the dental crown with the generally cylindrical neck portion of the abutment.

In certain embodiments, the cement is distributed through the plurality of vent holes after engaging the interior cavity of the dental crown with the generally cylindrical neck portion of the abutment.

In particular embodiments, the abutment is coupled to a dental implant via an abutment screw prior to coupling the dental crown to the abutment; the abutment screw comprises a first end configured to thread into the dental implant; the abutment screw comprises a second end opposite the first end; and the system further comprises a tapered insert configured to engage the second end of the abutment screw.

In some embodiments, the interior cavity of the dental crown and the generally cylindrical neck portion of the abutment form a margin when fully engaged; and a first portion of the cement is directed from the margin when the interior cavity of the dental crown and the generally cylindrical neck portion of the abutment are fully engaged. In particular embodiments, the first portion of the cement is less than 20 cubic millimeters. Some embodiments further comprise removing the first portion of the cement.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
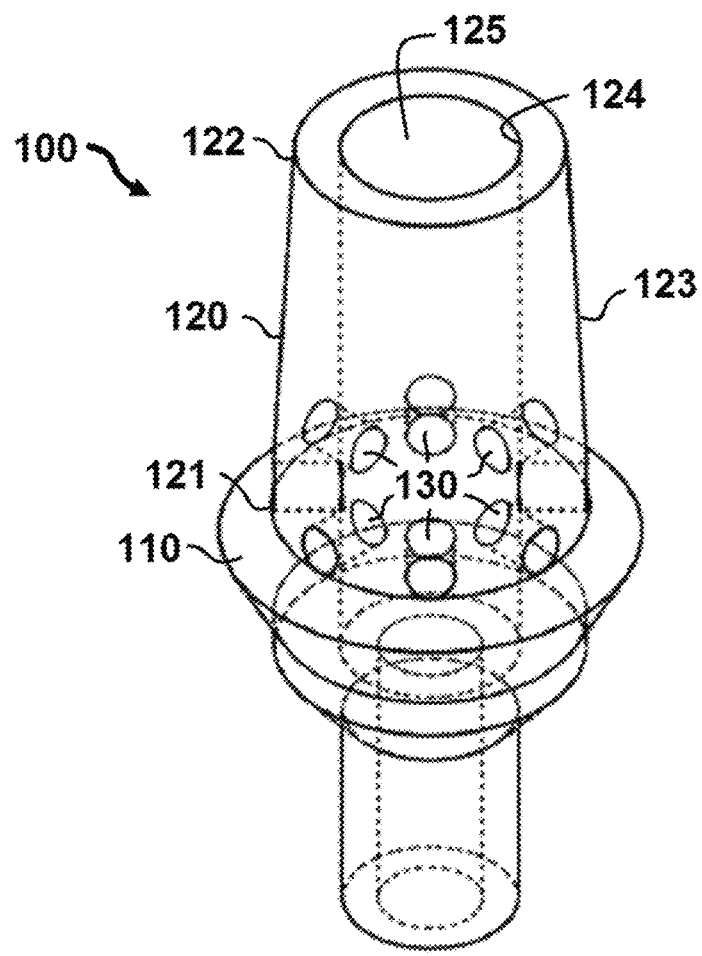
FIG. 1 illustrates a perspective view of an abutment device according to exemplary embodiments of the present disclosure.
Figure 2:
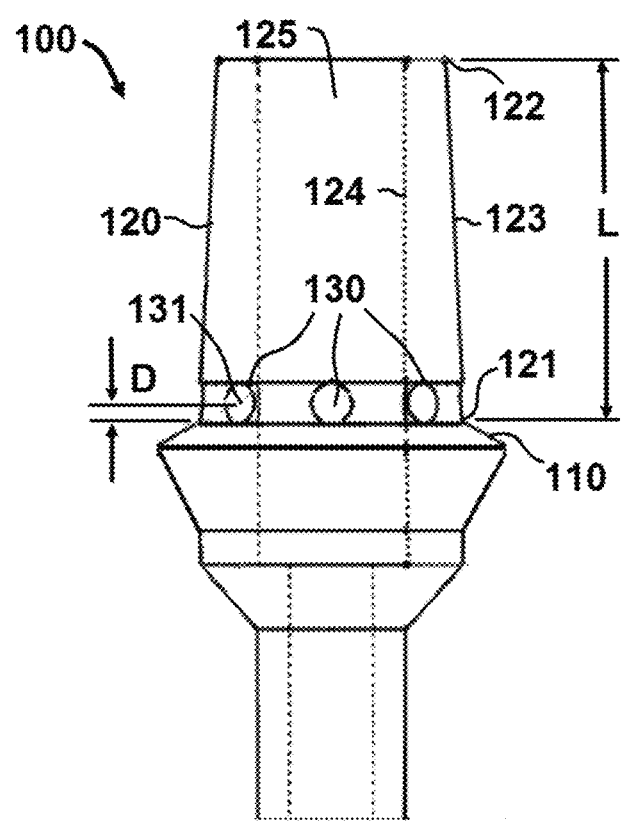
FIG. 2 illustrates a side view of the embodiment of FIG. 1.

Referring now to FIGS. 1-2 a dental abutment 100 comprises a base portion 110 and a generally cylindrical neck portion 120 extending from base portion 110. For purposes of clarity, not all of the features described herein are labeled in each figure. In the illustrated embodiment, generally cylindrical neck portion 120 comprises a first end 121 proximal to base portion 110 and a second end 122 distal from base portion 110. In the embodiment shown, generally cylindrical neck portion 120 further comprises an outer surface 123, as well as an inner surface 124 forming a central lumen 125. Generally, cylindrical neck portion 120 of dental abutment 100 also comprises a plurality of vent holes 130 extending from outer surface 123 to inner surface 124 and central lumen 125 in the illustrated embodiment. As shown in FIGS. 1-2, vent holes 130 are located proximal to base portion 110 of abutment 100 and are equally spaced around the circumference of neck portion 120. As explained in further detail below, the location of vent holes proximal to base portion 110 of dental abutment 100 provides significant benefits when mounting other components (e.g. a dental crown) to dental abutment 100.

In the embodiment shown in FIGS. 1-2, vent holes 130 are directly adjacent to base portion 110 of dental abutment 100 such that vent holes 130 are tangential to base portion 110 (e.g. the outer circumferences of vent holes 130 are tangential to base portion 110). It is understood that other embodiments may comprise an abutment with vent holes in a different location and configuration than those shown in FIGS. 1-2. For example, while the embodiment show in FIGS. 1-2 illustrates circular vent holes 130 directly adjacent base portion 110, other embodiments may comprise vent holes that are not circular and are proximal to the base portion but not directly adjacent.

As shown in FIG. 2, generally cylindrical neck portion 120 comprises a length L between first end 121 and second end 122. In certain embodiments, the distance D between first end 122 and a center 131 of a vent hole 130 is less than twenty percent of length L, and in specific embodiments distance D may be less than ten percent or five percent of length L. In particular embodiments, abutment 100 may comprise eight vent holes 130, where each of vent holes 130 may be configured as a circle with a diameter of 0.7 mm. Other embodiments may comprise a different number of vent holes or a vent holes with a different shape, including for example elliptical, square, rectangular or other polygonal shapes.

The embodiment shown in FIGS. 1-2 comprises cylindrical generally cylindrical neck portion 120 with a first end 121 that is larger in diameter than second end 122, such that outer surface 123 is tapered between the ends. As used herein, the term "generally cylindrical" comprises cylindrical shapes with one end that is up to ten percent larger than the opposing end (e.g. the diameter of the larger end is between 1.0 and 1.10 times the diameter of the smaller end).

In a typical dental crown seating, cement can be used to secure the crown to the abutment. During seating of a crown on a typical abutment, cement can be pushed from between the crown and abutment at the margin (e.g. the region near the base of the extended portion on which the crown is mounted). This can lead to issues as described elsewhere in this disclosure. In the embodiment disclosed herein, vent holes 130 can prevent or reduce the likelihood of residual excess cement from spilling into the soft tissue of the oral environment during the implantation of a cement-retained crown onto abutment 100.

Figure 3:
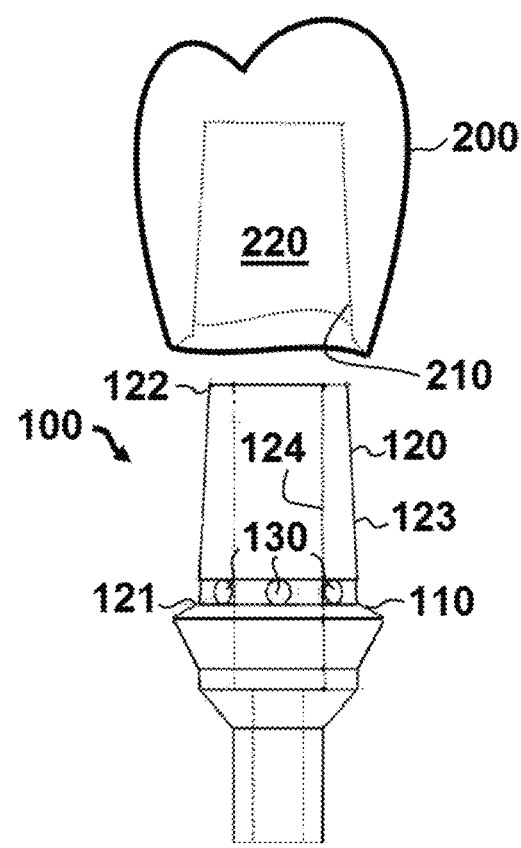
FIG. 3 illustrates a side view of the device of FIG. 1 and a dental crown prior to seating of the crown.
Figure 4:
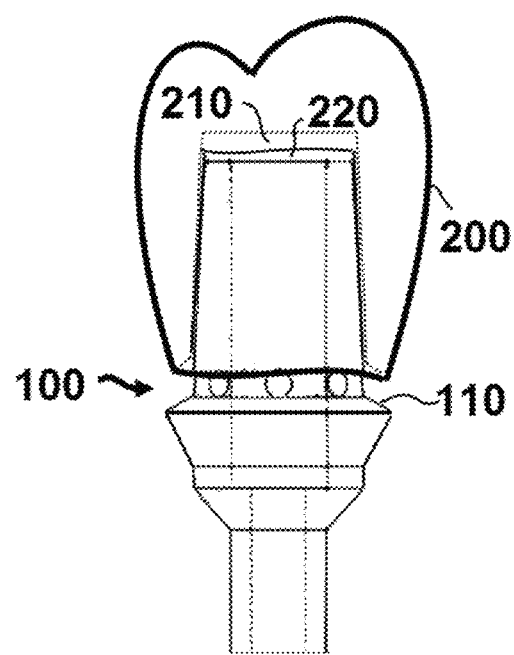
FIG. 4 illustrates a side view of the embodiment of FIG. 3 during seating of the crown.

Referring now to FIGS. 3-4 a crown 200 is shown during installation on abutment 100. In the embodiment shown, crown 200 comprises an interior cavity 210 configured to engage generally cylindrical neck portion 120. Prior to installation of crown 200, cement 220 can be placed in interior cavity 210. As crown 200 is pushed down onto abutment 100, cement 220 is distributed between the surfaces of interior cavity 210 and neck portion 120. In addition, cement 220 is forced toward first end 121 of neck portion 120. Without vent holes 130, excess cement 220 could be forced out from between crown 200 and abutment 100 as crown 200 is mounted. As noted elsewhere in this disclosure, such cement can be difficult to remove and can create undesirable consequences.

However, with vent holes 130 as shown in the illustrated embodiment, cement can be directed into and through vent holes 130 and between inner surface 124 and outer surface 123, rather than out from between crown 200 and abutment 100. This can significantly reduce the time and effort associated with seating of a crown and reduce the potential risks to the patient. The configuration of the vent holes 130 has also been determined to significantly affect the ability to minimize excess cement from being forced out from between crown 200 and abutment 100. For example, the location of vent holes 130 proximal to first end 121 of neck portion 120 is a significant factor in reducing or eliminating the amount of cement that is forced out from crown 200 during installation. As crown 200 is mounted on abutment 100, cement 220 is pushed from second end 122 of neck portion 120 towards first end 121. The clearances between interior cavity 210 and neck portion 120 are typically close, such that cement 220 is spread down neck portion 120 during seating.

If vent holes 130 were located in a region of neck portion 120 that is not proximal to first end 121, then cement 220 could be directed from between crown 200 and neck portion 120 during the later stages of seating of crown 200. For example, if vent holes 130 were located at the midpoint between first end 121 and second end 122, then the lower half of neck portion 120 would not permit excess cement 220 to be directed into the vent holes. Accordingly, any excess cement 220 that remained on the lower half of neck portion 120 would be directed from between crown 200 and neck portion 120. It is therefore important that vent holes 130 are positioned proximal to first end 121 (e.g. the location at which interior cavity 210 is fully engaged with neck portion 120 and crown 200 is fully engaged with abutment 100). In the embodiment shown, vent holes 130 are positioned directly adjacent first end 121 such that the circumference of individual holes is tangential to first end 121. As previously described, other embodiments may comprise vent holes that are proximal to first end 121 but not directly adjacent to first end 121.

The addition of vent holes 130 can also be used to more closely match the volume of interior cavity 210 in crown 200 and the available volume within abutment 100 (e.g. central lumen 125 and vent holes 130). Typical commercially available abutment geometries allow for up to approximately 90 cubic millimeters of dental cement when filled completely. However, a typical crown (press-fit) filled to the margin allows for approximately 135 cubic millimeters of dental cement. This discrepancy provides increased risk of excess cement being loaded into the system prior to implantation. The inclusion of vent holes as disclosed herein allows for a cement volume post-implantation, which closely mimics the final volume available considering the complete filling of the press-fit crown to the margin (e.g. completely filling interior cavity 210). In particular embodiments, abutments as disclosed herein can allow for volumes that closely match the interior cavity of the crown being seated (e.g. the volume of interior cavity 210) is between 1.0 and 1.2 times the combined volume of central lumen 125 and vent holes 130). This decreased discrepancy can allow dentists to be instructed to simply fill the crown to the margin with dental cement prior to seating the crown onto the abutment. This can minimize the amount of excess or residual cement that will be directed from the margin between crown 200 and abutment 100 and provide for a quick, easy cleanup while providing a full seal around the implant. In certain embodiments, the volume of excess cement that is directed from the margin will be less than 20 cubic millimeters.

Vent holes 130 can also provide other benefits to during the installation of crown 200. For example, vent holes 130 can reduce the likelihood that an air pocket or void could form between interior cavity 120 and neck portion 120 during installation. With vent holes 130 extending into central lumen 125, excess cement 220 can be directed into and through vent holes 130 (e.g. between inner surface 124 and outer surface 123), which can equalize the pressure throughout cement 220. This can reduce the possibility that air pockets may form in cement 220, particularly in the region near second end 122 of neck portion 120. The reduction in air pockets in cement 220 can increase the structural integrity of the bond between crown 200 and abutment 100.

The mechanical and structural integrity of the abutment 100 is also a consideration when determining the configuration vent holes 130. The inclusion of holes in neck portion 120 reduces the material in the cross-section and therefore potentially reduces the mechanical strength of neck portion 120 near vent holes 130. Locating vent holes 130 near proximal end 121 can minimize the reduction in mechanical strength of neck portion 120. For example, in the region near proximal end 121, the cross-sectional thickness of neck portion 120 (e.g. the distance between outer surface 123 and inner surface 124) is greater than the region near distal end 122). Locating vent holes 130 in this region where neck portion 120 is thicker (rather than thinner regions closer to second end 122) can reduce the likelihood of mechanical failure of abutment 100.

Figure 5:
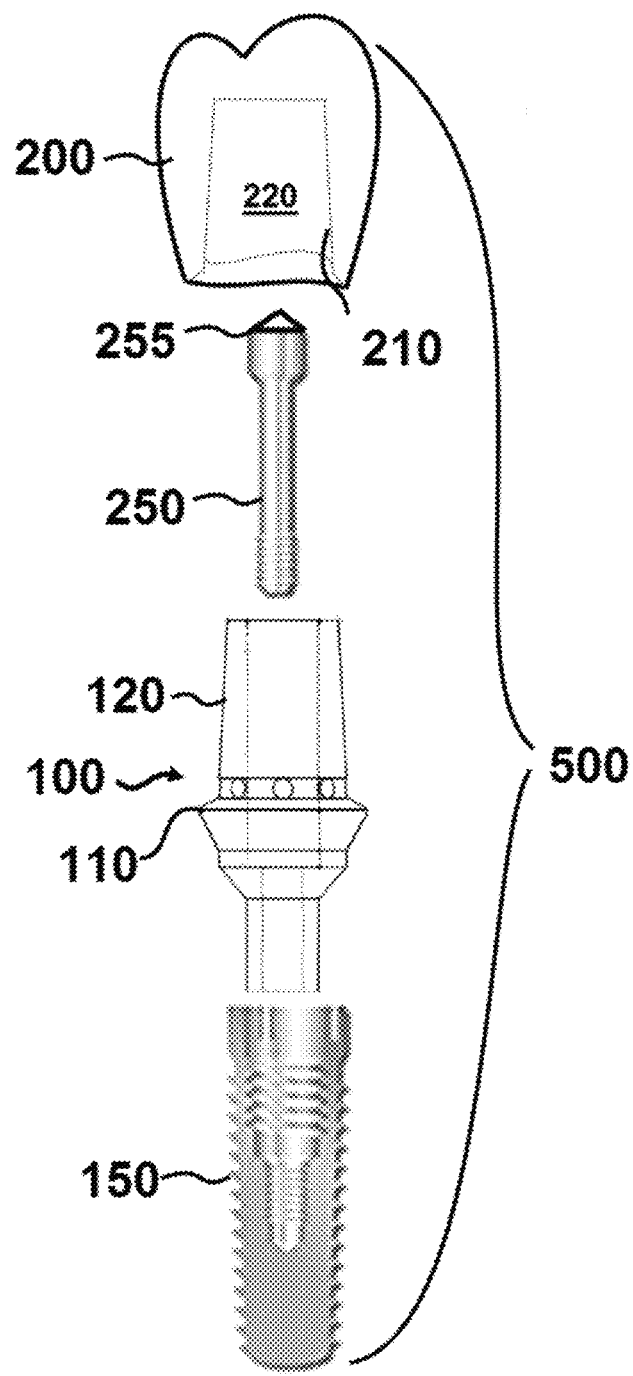
FIG. 5 illustrates a system comprising the embodiments of FIGS. 1-4 and an implant and an abutment screw.
Figure 6:
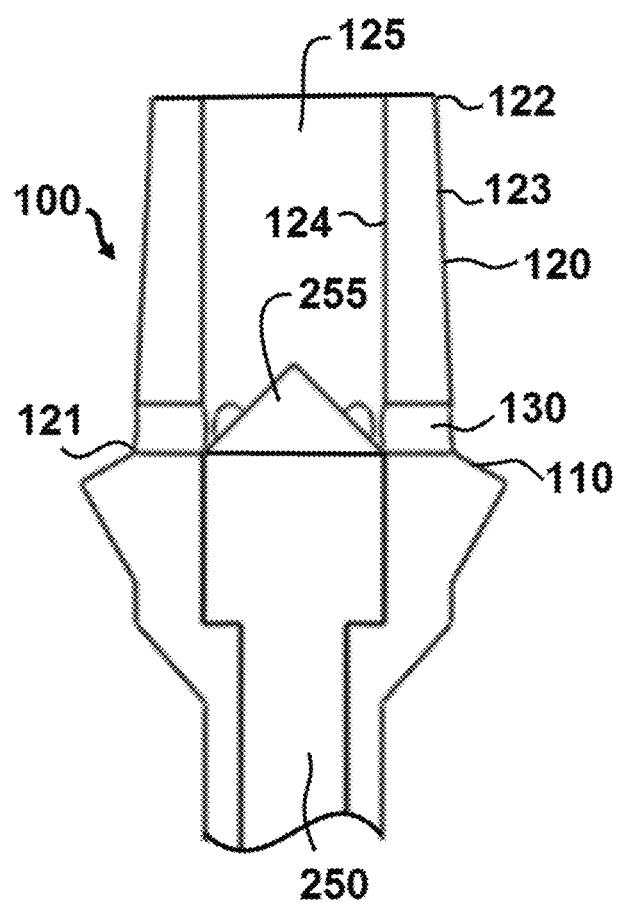
FIG. 6 illustrates a side view of the abutment device and abutment screw of FIG. 5.

Referring now to FIG. 5, in certain embodiments abutment 100 and crown 200 may be components in a dental implant system 500. In this embodiment, dental implant system 500 comprises abutment 100, crown 200, abutment screw 250 and implant 150. During use, implant 150 can be installed in bone tissue (e.g. the patient's jawbone) via a threaded connection. Abutment 100 can then be threaded into implant 150 via another threaded connection. While a threaded engagement for the abutment and implant is shown, it is understood that other embodiments may include an abutment and implant that are engaged via a friction fit. Abutment screw 250 can then be inserted through abutment 100 and threaded into implant 150 to further secure abutment 100 to implant 150. Crown 200 can then be mounted to abutment 100 with cement 220 (e.g. in the manner previously described in FIGS. 3-4). In certain embodiments, a tapered insert 255 can be coupled to abutment screw 250 (as shown in more detail in the section view of FIG. 6). Tapered insert 255 can assist in providing laminar flow of cement 220 during mounting of crown 200 on abutment 100.

Figure 7:
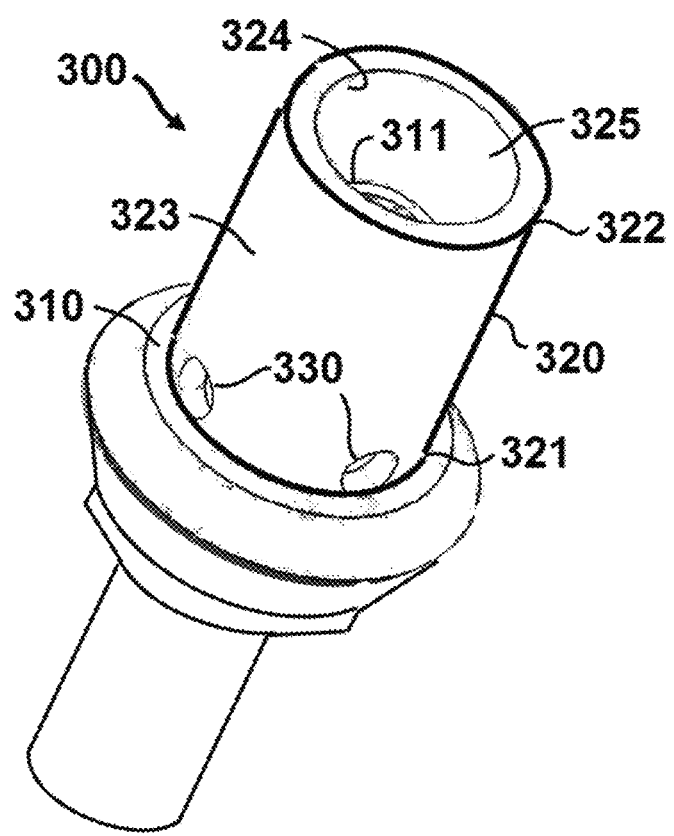
FIG. 7 illustrates a perspective view of an abutment device according to exemplary embodiments of the present disclosure.
Figure 8:
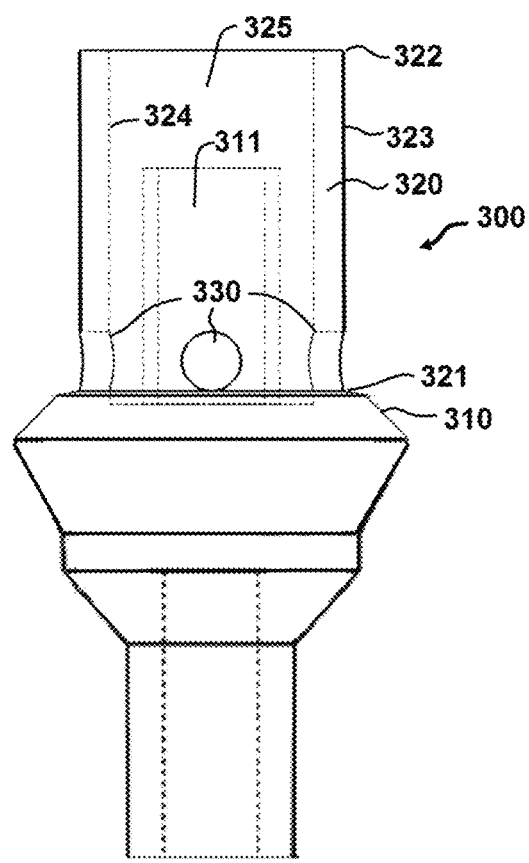
FIG. 8 illustrates a side view of the embodiment of FIG. 7.

Referring now to FIGS. 7-8, another embodiment of the present disclosure comprises an abutment 300 with a slightly different configuration than the previous embodiment. In this example, abutment 300 comprises a base portion 310 and a neck portion 320 that is cylindrical and does not taper from first end 321 to second end 322. Abutment 300 also comprises a plurality of vent holes 330 that extend from outer surface 323 to inner surface 324 and central lumen 325. In this embodiment, there are four vent holes 330 rather than the eight found in the previous embodiment, but it is understood that other embodiments may comprise a different number or configuration of vent holes. In addition, abutment 300 comprises an inner lumen 311 within central lumen 325. Abutment 300 is similar to abutment 100 in other respects, and functions in a manner equivalent to that described above for abutment 100.

Accordingly, exemplary embodiments of the present disclosure provide significant benefits and advantages as compared to existing devices and methods. Exemplary embodiments can provide numerous benefits in the mounting of a crown to a dental abutment, including reducing excess cement that may be forced out at the margin. This can reduce the time and effort needed to clean the excess cement and also reduce the likelihood of complications associated with excess cement. Furthermore, exemplary embodiments can improve the bond between the crown and abutment while minimizing any reduction in the mechanical properties of the abutment.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

1. (2004, May 12) Guidance for Industry and FDA Staff—Class II Special Controls Guidance Document: Root-form Endosseous Dental Implants and Endosseous Dental Abutments. Retrieved from http://www.fda.gov.
2. Agar J R, Cameron S M, Hughbanks J C, Parker M H. Cement removal from restorations luted to titanium abutments with simulated subgingival margins. Journal of Prosthetic Dentistry 1997; 78:43-47.
3. Allum S, Tomlinson R, Joshi R. The impact of loads on standard diameter, small diameter and mini implants: a comparative laboratory study. Clin. Oral Impl. Res. 2008. 19: 553-559.
4. American Academy of Periodontology. Peri-implant mucosities and peri-implantitis: a current understanding of their diagnosis and clinical implications. J Periodontol 2013; 84:436-443.
5. Anchieta R B, Machado L S, Hirata R, Bonfante E A, Coelho P G. Platform-switching for cement versus screwed fixed dental prosthesis: reliability and failure modes: an in vitro study. Clin Implant Dent Relate Res. 2015. doi: 10.1111/cid.12363.
6. Augthun M, Conrads G. Microbial findings of deep peri-implant bone defects. Int J Oral Maxillofac Implants 1997; 12:106-112.
7. Barnes, H. A. Measuring the viscosity of Large-particle (and flocculated) suspensions—A note on the necessary gap size rational viscometer. J. Non Newton. Fluid Mech. 2000, 94, 213-227.
8. Bassi M A, Bedini R, Pecci R, Loppolo P, Lauritano D, Carinci F. (2015) Mechanical properties of resin glass fiber-reinforced abutment in comparison to titanium abutment. J Indian Soc Periodontol. 19(3): 273-278.
9. Belser U, Buser D, Higginbottom F. Consensus statements and recommended clinical procedures regarding esthetics in implant dentistry. The International Journal of Oral & Maxillofacial Implants. 2004. 19: 73-74.
10. Belser U C, Schmid B, Higginbottom F, Buser D. Outcome analysis of implant restorations located in the anterior maxilla: a review of the recent literature. The International Journal of Oral & Maxillofacial Implants. 2004. 19: 30-42.
11. Biological evaluation of medical devices—Part 5: Tests for in vitro cytotoxicity. ISO 10993-5:2009. Geneva, Switzerland: ISO.

12. Biological evaluation of medical devices—Part 12: Sample preparation and reference materials. ISO 10993-12:2012. Geneva, Switzerland: ISO.
13. Biswas B K, Bag S, Pal S. Biomechanical analysis of normal and implanted tooth using biting force measurement. International Journal of Engineering and Applied Sciences. 2013. 4(2): 17-23.
14. Code of Federal Regulations (CFR). 2012. 29 C.F.R. 1910.1200 et seq. http://www.gpo.gov/fdsys/pkg/CFR-2012-title29-vol6/pdf/CFR-2012-title29-vol6-part1910-subpartZ.pdf.
15. Chaar M S, Att W, Strub J R. Prosthetic outcome of cement-retained implant-supported fixed dental restorations: a systematic review. J Oral Rehabil. 2011 September; 38(9):697-711.
16. Chun-Bo Tang, Si-Yu Liu, Guo-Xing Zhou, Jin-Hua Yu, Guang-Dong Zhang, Yi-Dong Bao and Qiu-Ju Wang. Nonlinear finite element analysis of three implant-abutment interface designs. International Journal of Oral Science. 2012. 4: 101-108.
17. Cornell L, Matthias K, Robert K. Evaluation of test protocol variables for dental implant fatigue research. Dental Materials. 2009. 25. 1419-1425.
18. Davies J E, Matsuda T. Extracellular matrix production by osteoblasts on bioactive substrata in vitro. Scanning Microsc 1998; 2:1445-1452.
19. Dentistry-Implants (2007) The International Organization for Standardization. ISO 14801.
20. Fransson C, Lekholm U, Jemt T, Berglundh T. Prevalence of subjects with progressive bone loss at implants. Clin Oral Implants Res 2005. 16: 440-446.
21. Gapski R, Neugeboren N, Pomeranz A Z, Reissner M W. Endosseous implant failure influenced by crown cementation: a clinical case report. Int J Oral Maxillofac Implants. 2008; 23(5):943-946.
22. Gaviria L, Salcido J P, Guda T, Ong J L. Current trends in dental implants. J Korean Assoc Oral Maxillofac Surg. 2014. 40(2): 50-60.
23. Gehrke, S A. (2013) Importance of Crown Height Ratios in Dental Implants on the Fracture Strength of Different Connection Designs: An In Vitro Study. Clinical Implant Dentistry and Related Research.
24. Graves D T, Oates T, Garlet G. Review of osteoimmunology and the host response in endodontic and periodontal lesions. Journal of Oral Microbiology. 2011. 3; 5304- DOI: 10.3402/jom.v3i0.5304.
25. Hamdan N M, Gray-Donald K, Awad M A, Johnson-Down L, Wollin S, Feine J S. Do implant overdentures improve dietary intake? A randomized clinical trial. J Dent Res. 2013 December; 92(12 Suppl):146S-53S
26. Hardy R, Cooper M S. Bone loss in inflammatory disorders. J Endocrinol 2009; 201:309
27. Hebel K S, Gajjar R C. Cement-retained versus screw-retained implant restorations: achieving optimal occlusion and esthetics in implant dentistry. J Prosthet Dent 1997; 77:28-35.
28. Higginbottom F, Belser U, Jones J D, Keith S E. Prosthetic management of implants in the esthetic zone. The International Journal of Oral & Maxillofacial Implants. 2004. 19: 62
29. Itakura Y, Kosugi N, Sudo H, Yamamoto S, Kumegawa M. Development of a new system for evaluating the biocompatibility of implant materials using an osteogenic cell line (MC3T3 E1). J Biomed Mater Res 1988; 22:613-622.
30. Javed F, Ahmed H B, Crespi R, Romanos G E. (2013) Role of primary stability for successful osseointegration of dental implants: Factors of influence and evaluation. Interv Med Appl Sci. 5(4): 162-167.
31. Korsch M, Robra B P, Walther W. Predictors of Excess Cement and Tissue Response to Fixed Implant-Supported Dentures after Cementation. Clin Implant Dent Relat Res. 2013 Jul. 24. doi: 10.1111/cid.12122.
32. Kumegawa M, Hiramatsu M, Hatakeyama K, Yajima T, Kodama H, Osaki T, Kurisu K. Effects of epidermal growth factor on osteoblastic cells in vitro. Calcif Tissue Int 1983; 35:542-548.
33. Lee C K, Karl M, Kelly J R. (2009) Evaluation of test protocol variables for dental implant fatigue research. Dental Materials. 25(11); 1419-1425.
34. Lee S Y, Kim S J, An H W, Kim H S, HA D G, Ryo K H, Park K B. (2015) The effect of the thread depth on the mechanical properties of the dental implant. J Adv Prosthodont. 7: 115-21.
35. Lindhe J, Berglundh T. The interface between the mucosa and the implant. Periodontol 2000 1998; 17:47-54.
36. Linkevicius T, Puisys A, Vindasiute E, Linkeviciene L, Apse P. Does residual cement around implant-supported restorations cause peri-implant disease? A retrospective case analysis. Clin Oral Implants Res. 2013; 24(11):1179-1184.
37. Linkevicius T, Vindasiute E, Puisys A, Peciuliene V. The influence of margin location on the amount of undetected cement excess after delivery of cement-retained implant restorations. Clinical Oral Implants Research. 2011. 22: 1379-1384.
38. Ma S. Fenton A. Screw-versus cement-retained implant prostheses: A systematic review of prosthodontic maintenance and complications. Int J prosthodont 2015; 28:127-45
39. Massoglia F, Catalan A, Martinez A, Flores M. (2016) Bending moments and failure of titanium and zirconia abutments with internal connections: In vitro study. Journal of Dental Health, Oral Disorders & Therapy. 4(1): 00095. DOI: 10.15406/jdhodt.2016.04.00095.
40. Mayta-Tovalino F R, Ccahuana-Vasquez V Z, Rosas-Diaz J C. (2015) Removal force of cast copings to abutments with three luting agents. Journal of Dental Implants. 5(1): 25
41. Mcallister B S, Leeb-Lundberg L M, Javors M A, Olson M S. Bradykinin receptors and signal transduction pathways in human fibroblasts: integral role for extracellular calcium. Arch Biochem Biophys 1993; 304:294-301.
42. Mcallister B S, Leeb-Lundberg L M, Olson M S. Bradykinin inhibition of egf- and pdgfinduced dna synthesis in human fibroblasts. Am J Physiol 1993; 265:c477-c484.
43. Menassa M, de Grandmont P, Audy N, Durand R, Rompre P, Emami E. Patients' expectations, satisfaction, and quality of life with immediate loading protocol. Clin Oral Implants Res. 2014 November 7
44. Modi R, Mittal R, Kohli S, Singh A, Sefa I. Screw versus cement retained prosthesis: a review. International Journal of Advanced Health Sciences. 2014. 1(6); 26-32.
45. Mombelli A, van Oosten M A C, Schurch E Jr, Lang N P. The microbiota associated with successful or failing osseointegrated titanium implants. Oral Microbiol Immunol 1987; 2:145-151.
46. Packer M, Nikitin V, Coward T, Davis D M, Fiske J. The potential benefits of dental implants on the oral health quality of life of people with Parkinson's disease. Gerodontology. 2009 March; 26(1):11-8.

47. Patel D, Invest J C, Tredwin C J, Setchell D J, Moles D R. An analysis of the effect of a vent hole on excess cement expressed at the crown-abutment margin for cement-retained implant crowns. J Prosthodont 2009; 18(1):54-59.
48. Pesqueira A A, Goiato M C, Filho H G, Monteiro D R, Santos D M, Haddad M F, et al. (2014) Use of stress analysis methods to evaluate the biomechanics of oral rehabilitation with implants. J Oral Implantol. 40: 217-28.
49. Pineyro A. One abutment-one time: the negative effect of uncontrolled abutment margin depths and excess cement—a case report. Compend Contin Educ Dent 2013; 34:680-4.
50. Quaresma S E T, Cury P R, Sendyk W R, Sendyk C. A finite element analysis of two different dental implants: stress distribution in the prosthesis, abutment, implant, and supporting bone. Journal of Oral Implantology. 2008. 34(1): 1-6.
51. Quirynen. Predisposing conditions for retrograde peri-implantitis, and treatment suggestions. Clin Oral Implants Res 2005; 16:599-608.
52. Ramer N, Wadhwani C, Kim A, Hershman D. Histologic findings within peri-implant soft tissue in failed implants secondary to excess cement: report of two cases and review of literature. N Y State Dent J. 2014; 80(2):43-46.
53. Raval N C, Wadhwani C P K, Jain S, Darveau R P. The interaction of implant luting cements and oral bacteria linked to peri-implant disease: an in vitro analysis of planktonic and biofilm growth—a preliminary study. Clinical Implant Dentistry and Related Research 2015; 17:1029-35.
54. Reddy S V, Reddy M S, Reddy C R, Pithani P, R S K, Kulkarni G. (2015) The influence of implant abutment surface roughness and the type of cement on retention of implant supported crowns. Journal of Clinical and Diagnostic Research. 9(3):ZC05-ZC07. doi:10.7860/JCDR/2015/12060.5621.
55. Renvert S, Polyzois L. Rick indicators for peri-implant mucositis: a systematic literature review. Journal of Clinical Periodontology. 2015. 42(S16): S172-S186.
56. Rodrigues D C, Valderrama P, Wilson T G Jr, Palmer K, Thomas A, Sridhar S, Adapalli A, Burbano M, Wadhwani C. Titanium corrosion mechanisms in the oral environment: a retrieval study. Materials 2013; 6(11):5258-5274.
57. Rodriguez L C, Saba J N, Chung K H, Wadhwani C, Rodrigues D C. In vitro effects of dental cements on hard and soft tissues associated with dental implants. Submitted to Journal of Prosthetic Dentistry. 2016a. Under Review.
58. Rodriguez L C, Saba J N, Meyer C, Chung K H, Wadhwani C, Rodrigues D C. A Finite Element Analysis of Novel Vented Dental Abutment Geometries for Cement-Retained Crown Restorations. Submitted to Clinical and Experimental Dental Research. 2016b. Under Review.
59. Rodriguez L C, Saba J N, Meyer C, Chung K H, Wadhwani C, Rodrigues D C. Mechanical evaluation of novel vented dental abutment. Submitted to Clinican and Experimental Dental Research. 2016c. Under Review.
60. Rompen E, Domken O, Degidi M, Pontes A E, Piattelli A. The effect of material characteristics, of surface topography and of implant components and connections on soft tissue integration: a literature review. Clin Oral Implants Res 2006; 17:55-67.
61. Roos-Jansaker A M, Lindahl C, Renvert H, Renvert S. Nine- to fourteen-year follow-up of implant treatment. part II: presence of peri-implant lesions. J Clin Periodontol 2006. 33: 290-295.
62. Saba J N, Rodriguez L C, Wadhwani C, Chung K H, Rodrigues D C. Effects of Cement-Retained Crown Abutment Designs on Cement Extrusion. Submitted to Journal of Dental Research. 2016. Under Review.
63. Santos G C, Santos M J M C. Selecting a temporary cement: a case report. Dentistrytoday.com, 2012. Web. 19 Oct. 2015. http://www.dentistrytoday.com/.
64. Scully C, Hobkirk J, Dios P D. J Oral Rehabil. Dental endosseous implants in the medically compromised patient. 2007 August; 34(8):590-9.
65. Schwedhelm E R, Lepe X, Aw T C. A crown venting technique for the cementation of implant-supported crowns. J prosthet dent. 2003. 89(1): 89-90.
66. Shelton R M, Rasmussen A C, Navies I E. Protein adsorption at the interface between charged polymer substrata and migrating osteoblasts. Biomaterials 1988; 9:24-29.
67. Sherif S, Susarla S M, Hwang J W, Weber H P, Wright R F. (2011) Clinician- and patientreported long-term evaluation of screw- and cement-retained implant restorations: a 5-year prospective study. Clin Oral Invest. 15: 993-999.
68. Shetty S, Garg A, Shenoy K K. Principles of screw-retained and cement-retained fixed implant prosthesis: a critical review. Journal of Interdisciplinary Dentistry. 2014. 4(3): 123-129.
69. Silva E, Felix S, Rodriguez-Archilla A, Oliveira P, dos Santos J M. (2014) Revisiting peri-implant soft tissue—histopathological study of the peri-implant soft tissue. Int J Clin Exp Pathol. 7(2): 611-618.
70. Squier R S, Agar J R, Duncan J P, Taylor T D. Retentiveness of dental cements used with metallic implant components. Int J Oral Maxillofac Implants 2001; 16:793-798.
71. Stawarczyk B, Basler T, Ender A, Roos M, Ozcan M, Hammerle C. (2012) Effect of surface conditioning with airborne-particle abrasion on the tensile strength of polymeric CAD/CAM crowns luted with self-adhesive and conventional resin cements. The Journal of Prosthetic Dentistry. 107(2): 94-101.
72. Strassburger Cl, Kerschbaum T, Heydecke G. Influence of implant and conventional prostheses on satisfaction and quality of life: A literature review. Part 2: Qualitative analysis and evaluation of the studies. Int J Prosthodont. 2006 July-August; 19(4):339-48.
73. Sudo H, Kodama H, Amagai Y, Yamamoto S, Kasai S. In vitro differentiation and calcification in a new clonal osteogenic cell line derived from newborn mous calcaria. J Cell Biol 1983; 96:191-198.
74. Tarica D Y, Alvarado V M, Truong S T. Survey of United States dental schools on cementation protocols for implant crown restorations. J Prosthet Dent. 2010. 103(2): 68-75.
75. Tarica D. Survey of United States dental schools on cementation protocols for implant crown restorations J Prosthet Dent 2010; 103:68-79.
76. Taylor T, Agar J R. Twenty years of progress in implant prosthodontics. J Prosthet Dent 2002; 88:89-95.
77. Titanium alloy guide. RMI Titanium Company. 2000: 1-48
78. Vieira R A, Melo A C, Budel L A, Gama J C, de Mattias Sartori I A, Thomé G. Benefits of rehabilitation with implants in masticatory function: is patient perception of change in accordance with the real improvement? J Oral Implantol. 2014 June; 40(3):263-9.
79. Wadhwani, C P K (ed.), Cementation in Dental Implantology: An Evidence-Based Guide, DOI 10.1007/978-3-642-55163-5_3, ©Springer-Verlag Berlin Heidelberg 2015
80. Wadhwani C P—Peri-implant disease and cemented implant restorations: a multifactorial etiology. Compend Contin Educ Dent 2013; 34:32-7.
81. Wadhwani C, Chung K H. Effect of modifying the screw access channels of zirconia implant abutment on the cement flow pattern and retention of zirconia restorations. J Prosthet Dent. 2014. 112(1):45-50.
82. Wadhwani C, Goodwin S, Chung K H. Cementing an Implant Crown: A Novel Measurement System Using Computational Fluid Dynamics Approach. Clin Implant Dent Relat Res 2014 Sep. 5. doi: 10.1111/cid.12258
83. Wadhwani C, Hess T, Pineyro A, Chung K H. Effects of abutment and screw access channel modification on dislodgement of cement-retained implant-supported restorations. Int J Prosthodont. 2013. 26(1):54-6.
84. Wadhwani C, Hess T, Pineyro A, Opler R, Chung K H. Cement application techniques in luting implant-supported crowns: a quantitative and qualitative study. The International Journal of Oral & Maxillofacial Implants. 2012. 27(4): 859-864.
85. Wadhwani C P, Pineyro A F. Implant cementation: clinical problems and solutions. Dent Today 2012; 31(1): 56-62.
86. Wadhwani C, Pineyro A, Technique for controlling the cement for an implant crown. Journal of Prosthetic Dentistry. 2009. 107: 57-58.
87. Wadhwani C, Piñeyro A, Hess T, Zhang H, Chung K H. Effect of implant abutment modification on the extrusion of excess cement at the crown-abutment margin for cement-retained implant restorations. Int J Oral Maxillofac Implants. 2011. 26(6): 1241-6.
88. Wadhwani C, Rapoport D, La Rosa S, Hess T, Kretschmar S. Radiographic detection and characteristic patterns of residual excess cement associated with cement-retained implant restorations: a clinical report. J Prosthetic Dentistry. 2011. 107(3). 151-157.
89. Wadhwani C P, Schwedhelm E R, Tarica D Y, Chung K H. Implant luting cements In: Cementation in dental implantology: An evidence based guide. Heidelberg. Springer science business media; 2015:47-82.
90. Wakabayashi N, Ona M, Suzuki T, Igarashi Y. Nonlinear finite element analyses: advances and challenges in dental applications. Journal of Dentistry. 2008. 36(7): 463-471.
91. Wang D, Christensen K, Chawla K, Xiao G, Krebsbach P H, Franceschi R T. Isolation and characterization of MC3T3-E1 preosteoblast subclones with distinct in vitro and in vivo differentiation/mineralization potential. J Bone Miner Res 1999; 14:893-903. 109
92. Weber H P, Kim D M, Ng M W, Hwang J W, Fiorellini J P. Peri-implant soft-tissue health surrounding cement- and screw-retained implant restorations: a multi-center, 3 year prospective study. Clin. Oral Impl. Res. 2006. 17; 375-379.
93. Wilson T G J. The positive relationship between excess cement and peri-implant disease: a prospective clinical endoscopic study. J Periodontol 2009; 80(9):1388-1392.
94. Wilson T G Jr, Valderrama P, Rodrigues D B. The Case for Routine Maintenance of Dental Implants. J Periodontol 2014; 85(5):657-660.
95. Wismeijer D. et al. Consensus statements and recommended clinical procedures regarding restorative materials and techniques for implant dentistry. Int J Oral Maxillofac Implants. 2014; 29 Suppl:137-40.
96. Wittneben J G, Millen C, Bragger U. Clinical performance of screw—versus cementretained fixed implant-supported reconstructions—a systematic review. Int J Oral Maxillofac Implants. 2014; 29 Suppl:84-98.
97. Zhao B, van der Mei H C, Subbiandoss G, de Vries J, Rustema-Abbing M, Kuijer R, Busscher H J, Ren Y. Soft tissue integration versus early biofilm formation on different dental implant materials. Dent Mater 2014; 30:716-27.
98. Zitzmann N U, Berglundh T. Definition and prevalence of peri-implant diseases. J Clin Periodontol. 2008. 35(8): 286-91.

The invention claimed is:
1. A dental abutment comprising: a base portion; a generally cylindrical neck portion extending from the base portion, wherein the generally cylindrical neck portion comprises: a first end proximal to the base portion; a second end distal from the base portion; an outer surface; and an inner surface forming a central lumen; and a plurality of vent holes extending from the outer surface of the generally cylindrical neck portion to the central lumen, wherein—the plurality of vent holes are located proximal to the base portion of the abutment; and the plurality of vent holes are directly adjacent to the base portion of the abutment, wherein the plurality of vent holes are tangential to the base portion of the abutment.
2. The dental abutment of claim 1 wherein:
the generally cylindrical neck portion comprises a length extending from the first end to the second end; and
a distance between the first end and a center of a vent hole in the plurality of vent holes is less than twenty percent of the length of the generally cylindrical neck portion.
3. The dental abutment of claim 1 wherein:
the generally cylindrical neck portion comprises a length extending from the first end to the second end; and
a distance between the first end and a center of a vent hole in the plurality of vent holes is less than ten percent of the length of the generally cylindrical neck portion.
4. The dental abutment of claim 1 wherein the plurality of vent holes comprises vent holes with a diameter between 0.5 mm and 1.0 mm.
5. The dental abutment of claim 1 wherein the plurality of vent holes comprises vent holes with a diameter between 0.6 mm and 0.9 mm.
6. The dental abutment of claim 1 wherein the plurality of vent holes comprises vent holes with a diameter of approximately 0.7 mm.
7. The dental abutment of claim 1 wherein the plurality of vent holes comprises at least four vent holes.
8. The dental abutment of claim 1 wherein the plurality of vent holes comprises at least eight vent holes.
9. The dental abutment of claim 1 wherein:
the first end of the generally cylindrical neck portion has a first diameter;
the second end of the generally cylindrical neck portion has a second diameter; and
the first diameter is between 1.0 and 1.10 times the second diameter.
10. A system comprising:
an abutment according to claim 1;
a dental implant;
an abutment screw configured to couple the abutment to the dental implant; and
a crown configured to couple to the abutment.

11. The system of claim 10, wherein:
the abutment screw comprises a first end configured to thread into the dental implant;
the abutment screw comprises a second end opposite the first end; and
the system further comprises a tapered insert configured to engage the second end of the abutment screw.

12. The system of claim 10, wherein: the crown comprises an interior cavity having a first volume; the central lumen and the plurality of vent holes have a second combined volume; and the first volume is between 1.0 and 1.2 times the second combined volume.

13. A method of coupling a dental crown to an abutment, the method comprising:
obtaining a dental crown comprising an interior cavity;
placing cement in the interior cavity of the dental crown; and
coupling the dental crown to an abutment according to claim 1 by engaging the interior cavity of the dental crown with the generally cylindrical neck portion of the abutment.

14. The method of claim 13 wherein the cement is distributed through the plurality of vent holes after engaging the interior cavity of the dental crown with the generally cylindrical neck portion of the abutment.

15. The method of claim 14 wherein:
the abutment is coupled to a dental implant via an abutment screw prior to coupling the dental crown to the abutment;
the abutment screw comprises a first end configured to thread into the dental implant;
the abutment screw comprises a second end opposite the first end; and
the system further comprises a tapered insert configured to engage the second end of the abutment screw.

16. The method of claim 13 wherein:
the interior cavity of the dental crown and the generally cylindrical neck portion of the abutment form a margin when fully engaged; and
a first portion of the cement is directed from the margin when the interior cavity of the dental crown and the generally cylindrical neck portion of the abutment are fully engaged.

17. The method of claim 16 wherein the first portion of the cement is less than 20 cubic millimeters.

18. The method of claim 16 further comprising removing the first portion of the cement.

* * * * *